United States Patent
Yamamoto et al.

(10) Patent No.: US 7,604,776 B2
(45) Date of Patent: Oct. 20, 2009

(54) SAMPLE-LIQUID ANALYSIS DISC AND METHOD FOR ANALYZING SAMPLE MIXTURE LIQUID

(75) Inventors: Tomohiro Yamamoto, Osaka (JP); Toshihiko Yoshioka, Osaka (JP); Nobuhiko Ozaki, Kanagawa (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/113,643

(22) Filed: May 1, 2008

(65) Prior Publication Data

US 2008/0227217 A1  Sep. 18, 2008

Related U.S. Application Data

(63) Continuation of application No. PCT/JP2006/321731, filed on Oct. 31, 2006.

(30) Foreign Application Priority Data

Nov. 1, 2005 (JP) ............................ 2005-318405
Nov. 2, 2005 (JP) ............................ 2005-319715

(51) Int. Cl.
*G01N 35/00* (2006.01)
*G01N 35/08* (2006.01)

(52) U.S. Cl. .............................. 422/58; 422/50; 422/56; 422/57; 422/61; 422/64; 422/72; 436/45; 436/177; 435/287.3; 435/287.9; 435/288.7

(58) Field of Classification Search ........................ None
See application file for complete search history.

(56) References Cited

U.S. PATENT DOCUMENTS

| 4,515,889 | A | * | 5/1985 | Klose et al. ..................... 435/4 |
| 5,122,284 | A |   | 6/1992 | Braynin et al. |
| 5,413,732 | A |   | 5/1995 | Buhl et al. |
| 6,063,589 | A | * | 5/2000 | Kellogg et al. ................ 435/24 |
| 2006/0013741 | A1 | * | 1/2006 | Nadler ....................... 422/100 |
| 2006/0057740 | A1 |   | 3/2006 | Hiroshi et al. |
| 2007/0280857 | A1 | * | 12/2007 | Song et al. .................. 422/100 |

FOREIGN PATENT DOCUMENTS

| WO | WO 93/04195 A1 | 8/1991 |
| WO | WO 00/26677 A1 | 5/2000 |
| WO | WO 00/40750 A1 | 7/2000 |

* cited by examiner

*Primary Examiner*—P. Kathryn Wright
(74) *Attorney, Agent, or Firm*—McDermott Will & Emery LLP

(57) ABSTRACT

A reaction of a sample mixture liquid is detected accurately, by allowing a solid reagent to be dissolved and reacted in a liquid sample quickly and accurately. A disc main body, and at least one sample mixing unit provided at the disc main body are provided, and the sample mixing unit is provided with: a liquid sample reserve unit; a reagent chamber capable of disposing a plurality of the solid reagents; and a measurement chamber to which a sample mixture liquid containing a liquid sample and a solid reagent mixed in the reagent chamber is supplied. The reagent chamber has a form which allows a plurality of the solid reagents to be disposed in the direction substantially parallel to the radial direction of the disc in which centrifugal force is generated, or in the direction substantially perpendicular to the radial direction of the disc.

10 Claims, 8 Drawing Sheets

F I G. 5
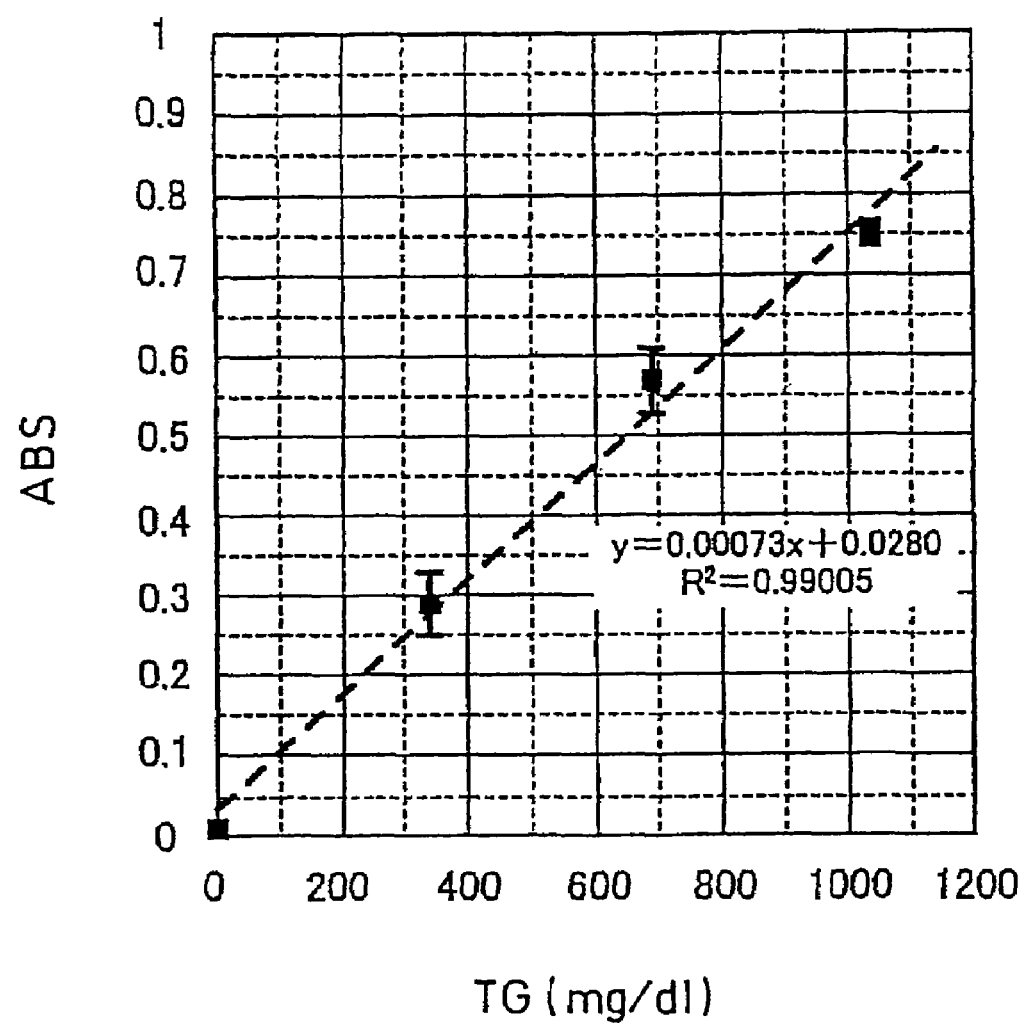

F I G. 1 0
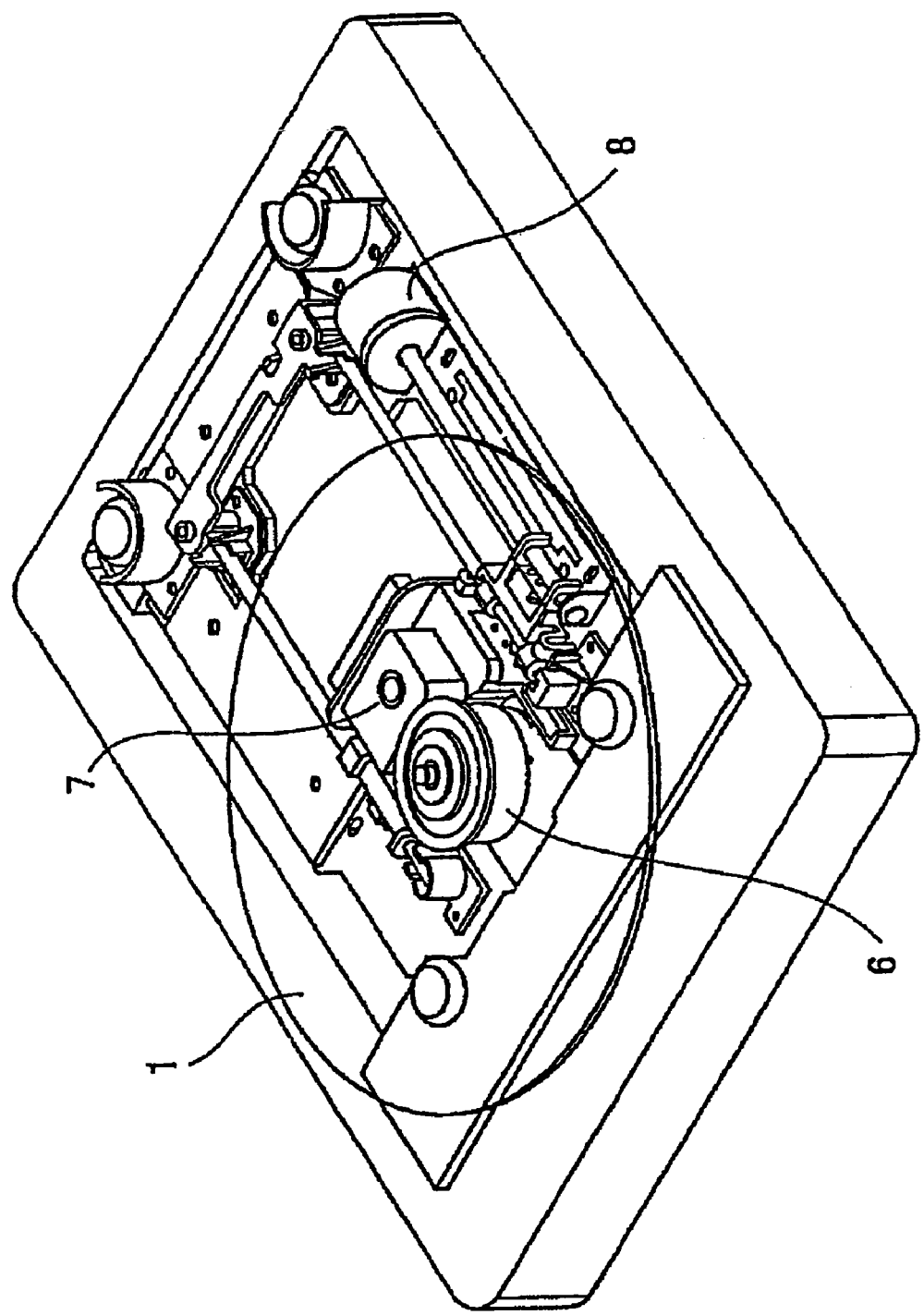

F I G. 1 1
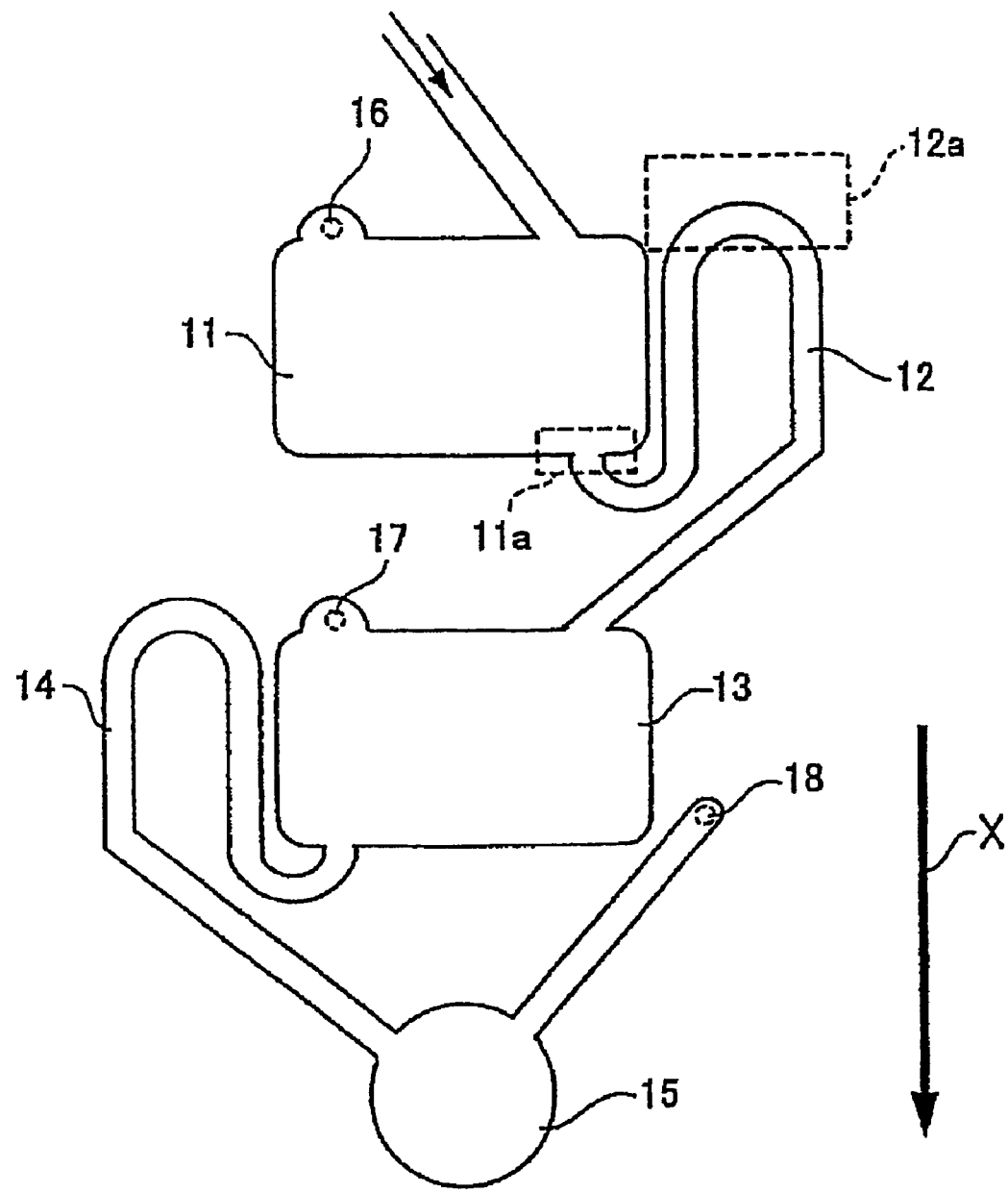

US 7,604,776 B2

SAMPLE-LIQUID ANALYSIS DISC AND METHOD FOR ANALYZING SAMPLE MIXTURE LIQUID

RELATED APPLICATIONS

This application is a continuation of International Application No. PCT/JP2006/321731, whose international filing date is Oct. 31, 2006 which in turn claims the benefit of Japanese Patent Application No. 2005-318405, filed on Nov. 1, 2005, and Japanese Patent Application No. 2005-319715, filed on Nov. 2, 2005, the disclosures of which Applications are incorporated by reference herein.

TECHNICAL FIELD

The present invention relates to a sample-liquid analysis disc for analyzing a sample by mixing a liquid sample supplied into the disc main body with a solid reagent disposed in the disc main body, and by detecting a chemical reaction of the sample mixture liquid thus obtained; and to a method for analyzing a sample mixture liquid.

BACKGROUND ART

With the advancement of assay, analysis, and examination techniques in recent years, various substances have been becoming measurable. Particularly, in the field of clinical examination, with the development of measurement principle based on specific reactions such as biochemical reaction, enzyme reaction, or immune reaction, substances in body fluids that reflect on condition of a disease became measurable.

Point of Care Testing (POCT) has been receiving attention particularly. POCT aims for simple and quick measurement in the first place, and for reduction in time it takes from sample taking to obtaining examination result. Therefore, for POCT, simple measurement principle is necessary. Also, there has been a demand for a measurement device which is small, easy-to-carry, and easy-to-operate.

In recent measurement devices for POCT, simple measurement principle has been developed. With such developments, techniques for solidifying a biological component, sensor device making, sensor system making, microfabrication, and micro fluid control are advancing. Thus, highly practical measurement devices have been increasingly provided.

For such measurement devices for POCT, for example, Patent Document 1 has proposed a device for qualitative and quantitative analysis of a sample supplied on the disc. The measurement device of Patent Document 1 is described with reference to FIG. FIG. 9 is a schematic cross sectional view of a portion of a chamber in an analysis disc. The disc 1 is provided with the sample supply hole 2 and the flow path 3 communicating with the sample supply hole 2. To the flow path 3, the reagent 4, which changes its optical property (transmittance, color, and the like) by reacting with the sample 5, is applied. The sample 5 is supplied from the sample supply hole 2 into the disc 1 and then analysis is carried out.

FIG. 10 is a schematic perspective view of an analysis device using the disc 1 of above, with a partially transparent view. Configuration of this analysis device is similar to the so-called optical disc device, the analysis device comprising the spindle motor 6 for spinning the disc 1; the optical pick-up 7 for applying a light beam to the sample 5 supplied and spread in the disc 1 or to the reagent 4 reacted with the sample 5; and the feed motor 8 for moving the optical pick-up 7 in the radial direction of the disc 1.

The disc 1 mounted in the analysis device is spun by the spindle motor 6. The sample 5 is supplied and spread in the flow path 3 of the disc 1 with the centrifugal force, to react with the reagent 4 applied in the flow path 3. After the reaction, a light beam is applied to the sample 5 or the reagent 4 in the flow path 3 by the optical pick-up 7, while the disc 1 is being spun. By detecting the reflected light or transmitted light of the light beam, reaction of the reagent is analyzed.

Patent Document 2 has proposed, for example, providing a flow path for connecting a plurality of chambers to which the reagent is applied in the disc. In this way, function of moving and stopping the sample mixture liquid freely between the chambers can be added to the disc. Thus, a plurality of reagents can be dissolved and reacted in order.

The sample-liquid analysis disc having a configuration of a microfluid device, proposed by Patent Document 2, is described briefly with reference to FIG. FIG. 11 is a diagram prepared by the inventors of the present invention for describing the technique described in Patent Document 2. FIG. 11 is a schematic view illustrating a relevant part of the disc included in the device proposed in Patent Document 2, in the direction of the normal to the main surface of the sample-liquid analysis disc. In FIG. 11, the flow path 12, bending, is connected to the lower side 11a of the upstream-side chamber 11, relative to centrifugal force direction X of the disc. The bending portion 12a of the flow path 12 is located at a position higher than the upper-side wall face, relative to centrifugal force direction X of the upstream-side chamber 11. The flow path 12 downstream of the bending portion 12a extends downward relative to centrifugal force direction X, and connected to the downstream-side chamber 13.

The downstream-side chamber 13 is connected to the transmitted light measurement chamber 15 by the flow path 14, also bending similarly to the flow path 12. The depth of the upstream-side chamber 11 in the direction of normal to the main surface is larger than the depth of the flow path 12. Thus, the sample mixture liquid that has been moving toward the downstream-side chamber 13 in the flow path 12 with capillarity accumulates at the portion where the flow path 12 is connected to the downstream-side chamber 13. As a result, the sample mixture liquid headed from the upstream-side chamber 11 to the downstream-side chamber 13 can be stopped at the point right before the downstream-side chamber 13.

By applying the centrifugal force by spinning the disc under such condition, the sample mixture liquid standing still flows into the downstream-side chamber 13. The bending portion 12a of the flow path 12 is located at a position higher than the upper-side wall face as noted above, relative to centrifugal force direction X of the upstream-side chamber 11. The flow path 12 downstream of the bending portion 12a extends downward, relative to the centrifugal force direction. With such a configuration, when the centrifugal force is applied, siphon effect comes into play on the sample mixture liquid accumulated in the upstream-side chamber 11 and filling the flow path 12 up to the point right before the downstream-side chamber 13, and almost all amount of the sample mixture liquid accumulated in the upstream-side chamber 11 flows into the downstream-side chamber 13 via the flow path 12.

While the centrifugal force is in effect, the sample mixture liquid that flowed into the downstream-side chamber 13 also flows into the flow path 14, but when seen in centrifugal force direction X, the liquid level in the flow path 14 and the liquid level in the downstream-side chamber 13 are the same.

Thus, as in the case of the flow path 12 described above, when the bending portion (not shown) of the flow path 14 is located at a position higher than the upper-side wall face of the downstream-side chamber 13, while the centrifugal force is in effect, the sample mixture liquid does not move to the point right before the next chamber (transmitted light measurement chamber 15).

The centrifugal force effect is lost when the spinning of the disc is stopped. At this time, from the flow path 14, the sample mixture liquid reaches the point right before the transmitted light measurement chamber 15 by capillarity. When the disc starts spinning again afterwards, with the effect of the centrifugal force, the sample mixture liquid flows into the transmitted light measurement chamber 15.

When the spinning of the disc (centrifugal force effect) is stopped, the sample mixture liquid in the transmitted light measurement chamber 15 may flow backward into the flow path 14 by capillarity. The backflow causes the amount of the sample mixture liquid in the transmitted light measurement chamber 15 to be insufficient; therefore, the centrifugal force is brought into effect by spinning the disc also when measuring the transmitted light.

For smooth flow of the sample mixture liquid into the chambers 11, 13, and 15, air holes 16, 17, and 18 are provided, at an upper portion (relative to centrifugal force direction X) of each of the chambers 11, 13, and 15 where the sample mixture liquid does not reach. In this way, the sample mixture liquid and the reaction reagent can be sufficiently dissolved and reacted. Also, the smooth movement of the sample mixture liquid can also be achieved in the flow path.

The reaction reagent necessary for the measurement of the specific component in the sample mixture liquid is carried in the upstream-side chamber 11, for example by drying. In this case, a reaction reagent layer is formed, by dropping and drying the aqueous solution of the reagent having at least a reagent concentration necessary for the reaction in a volumetric capacity of the upstream-side chamber 11; or by dropping and drying the aqueous solution of the reagent in an amount and a concentration that allow the reagent to be carried in an amount necessary for the reaction in the upstream-side chamber 11 when the reaction reagent is dissolved in the sample mixture liquid of an amount of the volumetric capacity of the upstream-side chamber 11.

It has also been proposed that the reaction reagent is solidified by freeze-drying the reagent solution, to improve solubility. For example, Patent Document 3 has proposed dropping the reagent solution in a refrigerating agent such as liquid nitrogen to obtain a spherical frozen material, and freeze-drying the spherical frozen material, to obtain homogenous reagent granules.

Patent Document 4 has proposed removing hemocyte by centrifugal separation in a blood measurement, to allow only the plasma component in blood to react with the reagent. The device described in Patent Document 4 has a function of separating plasma from whole blood by centrifugal force, and has a rotor for centrifugal separation, an inner chamber, a plurality of concave portions for testing, and a pathway. By disposing for example spherical granular reagent in the rotor for centrifugal separation, quick dissolution of reagent, that is, excellent reactivity can be achieved. For the reagent, in view of shelf life, granular reagent formed by freeze-drying can also be used.

With this device, a liquid sample can be supplied in stages. In this way, the measurement can also be carried out for the case when a plurality of reactions between the solid reagent and the liquid sample are carried out not simultaneously but in stages, and when the solid reagent has to be used in a plurality of kinds.

Patent Document 1: WO0026677

Patent Document 2: Japanese Unexamined Patent Publication No. 2002-534096

Patent Document 3: Japanese Patent No. 3187835

Patent Document 4: U.S. Pat. No. 5,122,284

DISCLOSURE OF THE INVENTION

Problem to be Solved by the Invention

In the device proposed in Patent Document 2, the reagent layer is formed in the upstream-side chamber 11, by wind-drying the reagent solution. However, with such a reagent layer, although the sample mixture liquid flows into the chamber, no effect of stirring can be achieved, and sometimes the reagent layer is not dissolved sufficiently. That is, the chemical reaction necessary for the measurement may not advance sufficiently. Also, when the reagent layer is obtained by wind-drying the reagent solution, the reagent layer surface becomes high in density. This also is a factor that prevents the reagent layer from being dissolved in the sample mixture liquid. Further, in the process of wind-drying the reagent solution, evaporation of water causes the reagent solution to be highly condensed. Thus, depending upon the reagent layer composition, sometimes it may be denatured.

When a plurality of kinds of granular reagents that are preferably prevented from being mixed together in terms of storage characteristics are used in the device proposed in Patent Document 4, compared with the case when a single granular reagent is used, the volume of each granular reagent needs to be made smaller relative to the amount of liquid sample for dissolving the granular reagent.

For example, to allow two granular reagents to be dissolved and reacted simultaneously, the volume of each of the granular reagents has to be half of the sample mixture liquid amount or less. Thus, the density of the granular reagent increases, thereby decreasing solubility of the granular reagent. The granular reagent may be disposed individually at separate chambers, and a pathway for connecting the chambers may be provided, so that the sample mixture liquid dissolves the granular reagents one by one. However, by disposing a plurality of chambers, measurement steps increase, making the entire measurement time longer.

In view of the conventional techniques described above, the present invention aims to provide a sample-liquid analysis disc which is capable of quickly and accurately dissolving the solid reagent in the liquid sample and allowing them to react, and detecting the reaction of the sample mixture liquid accurately; and a method for analyzing a sample mixture liquid.

Means for Solving the Problem

The present invention relates to a sample-liquid analysis disc for analyzing a sample mixture liquid containing a liquid sample and a solid reagent by detecting a chemical reaction between the liquid sample and the solid reagent, the sample-liquid analysis disc comprising:

a disc main body and at least one sample mixing unit provided at the disc main body, wherein the sample mixing unit comprises:

a liquid sample reserve unit for reserving the liquid sample;

a reagent chamber, which is connected to the liquid sample reserve unit via a first flow path, and formed so that a plurality of the solid reagents can be disposed, and to which the liquid sample is supplied, from the liquid sample reserve unit via the first flow path by centrifugal force caused by at least a spin of the disc main body;

a measurement chamber, which is connected to the reagent chamber via a second flow path, and to which the sample mixture liquid containing the liquid sample and the solid reagent mixed in the reagent chamber is supplied by centrifugal force caused by the spin of the disc main body and capillarity generated in the second flow path;

wherein the reagent chamber is formed so that the plurality of the solid reagents can be disposed, in the direction substantially parallel to the radial direction of the disc in which the centrifugal force is generated, or in the direction substantially perpendicular to the radial direction.

The "solid reagent" in the present invention is a solidified reagent necessary for the reaction. The form of the reagent is not particularly limited, as long as the reagent can be disposed in the reagent chamber in an amount necessary for the reaction. For example, the form may be any of semi-spherical, spherical, cylindrical, and polyhedron. The method for manufacturing the solid reagent is not particularly limited, as long as the solid reagent as described above can be obtained. For example, the solid reagent may be obtained by filling the powder of the reagent forming the solid reagent in a mold having a predetermined form, and compressing the powder. The solid reagent may also be obtained by dropping an aqueous solution containing the reagent forming the solid reagent, and freeze-drying the aqueous solution while controlling to give a diameter of an arbitrary size to the solid reagent.

In this way, with the centrifugal force that works on the disc main body and the capillarity in the reagent chamber, the liquid sample and the solid reagent are mixed further reliably. Thus, there is no need to lessen the volume of each solid reagent relative to the volume of the liquid sample for dissolving the solid reagent.

The reagent chamber is preferably substantially rectangular having a long side and a short side when seen in the direction of normal to the disc main surface, and preferably formed so that the long side is substantially parallel to the radial direction.

The reagent chamber may also be formed so that the reagent chamber is substantially rectangular having a long side and a short side when seen in the direction of normal to the disc main surface, and the long side is substantially perpendicular to the radial direction.

The solid reagent is preferably fixed in the reagent chamber.

In this way, the capillarity is allowed to work between the reagent chamber and the solid reagent further reliably. Thus, with the centrifugal force that works on the disc main body and the capillarity, the solid reagent in the reagent chamber is allowed to be dissolved completely, and the reaction time can be shortened.

In the reagent chamber, at least a portion of the solid reagent is preferably fixed in the direction of normal to the disc main surface. For example, the height of the internal portion of the reagent chamber may be made equal to or less than the height of the solid reagent, to sandwich the solid reagent between the upper side and the lower side of the reagent chamber in the direction of normal to the disc main surface.

In the plane direction of the disc main surface, the length of the short side of the substantially rectangular reagent chamber may also be made equal to or less than the width of the solid reagent.

Further, at least a portion of the inner wall of the reagent chamber may be formed so that its cross section has a concave shape, to prevent a gap at the portion where the solid reagent contacts the inner wall when the solid reagent is disposed.

In this way, cracks or chipping of the solid reagent can be prevented when the solid reagent having a curved face is disposed in the reagent chamber.

In the reagent chamber, a plurality of the solid reagents is preferably disposed.

The solid reagent is preferably formed of freeze-dried granules.

In this way, the surface area of the solid reagent can be made larger. Thus, the solid reagent can be made further easily dissolved in the liquid sample.

The present invention also provides a method for analyzing a sample mixture liquid using the above sample-liquid analysis disc, the method comprising:

supplying a liquid sample to the liquid sample reserve unit in a volume corresponding to a volume of one solid reagent;

supplying the liquid sample from the liquid sample reserve unit to the reagent chamber based on centrifugal force by spinning a disc main body;

mixing the liquid sample and the solid reagent in the reagent chamber by using the centrifugal force and capillarity; and supplying the sample mixture liquid into the measurement chamber, to detect a chemical reaction of the sample mixture liquid in the measurement chamber.

In the process of dissolving the solid reagent in the liquid sample, a portion of each of the solid reagents is dissolved when the liquid sample flows into the reagent chamber, and then with the centrifugal force that works on the disc main body and capillarity, the solid reagent left undissolved can also be dissolved completely. In this way, the reaction time can be shortened. As a result, the chemical reaction of the sample mixture liquid can be accurately detected.

The detection is preferably carried out optically. For example, by detecting the amount of the transmitted light or changes in the absorbance in the sample mixture liquid, a chemical reaction of the sample mixture liquid can be detected highly accurately.

EFFECT OF THE INVENTION

The present invention provides a sample-liquid analysis disc and a method for analyzing a sample mixture liquid, which enable quick and accurate dissolution and reaction of a solid reagent in a liquid sample, and accurate detection of the reaction of the sample mixture liquid.

BRIEF DESCRIPTION OF THE DRAWINGS

FIG. 5 A diagram illustrating changes in absorbance dependent on the TG concentration of a sample mixture liquid in one embodiment of the present invention.

FIG. 10 A schematic perspective view of a sample mixture liquid analysis device using a conventional disc, with a partially transparent view.

FIG. 11 A schematic view illustrating a relevant part of the disc, in the direction of normal to the main surface of the conventional sample-liquid analysis disc.

BEST MODE FOR CARRYING OUT THE INVENTION

Embodiment 1

In the following, embodiments of the present invention are described by referring to FIGs.

Figure 1:
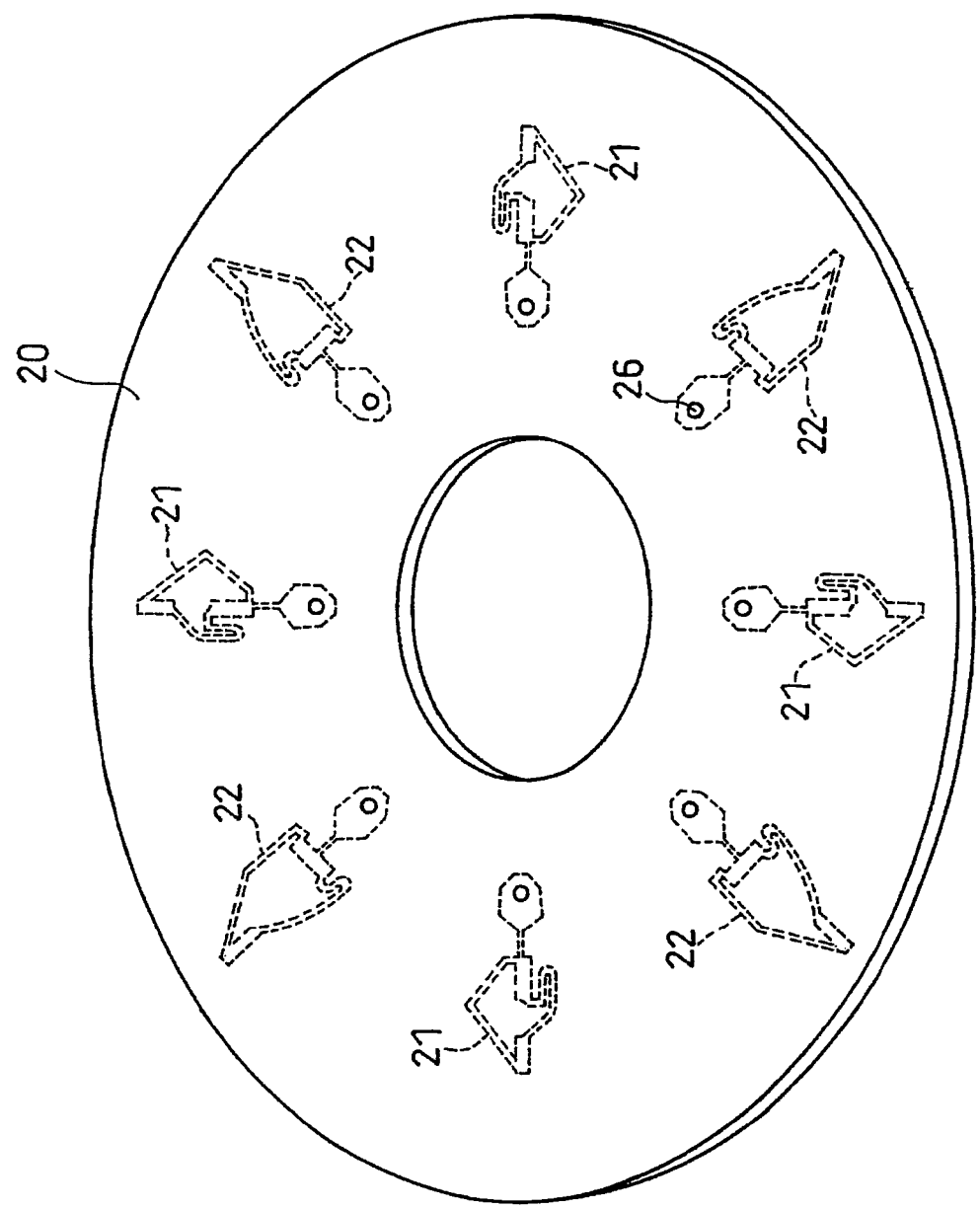
FIG. 1 A diagram illustrating a configuration of an embodiment of a sample-liquid analysis disc of the present invention.

First, a structure of a sample-liquid analysis disc in the present invention is described by referring to FIGs. FIG. 1 is a schematic diagram illustrating a configuration of a sample-liquid analysis disc in an embodiment of the present invention. In FIG. 1, a disc main body 20 of the sample-liquid analysis disc includes a plurality of sample mixing units 21 and 22. In the sample mixing unit 21, with centrifugal force and capillarity in the disc, a liquid sample is supplied to each chamber in a stepwise fashion. With a diameter of 80 to 120 mm, the disc main body 20 can secure an enough area for disposing, as mentioned later, each flow path and each chamber to be disposed in series in the direction of the disc diameter. Such a size is about the same as the size of commercially available CDs. Therefore, such a size is preferable in that it renders the disc handling easy.

Figure 2:
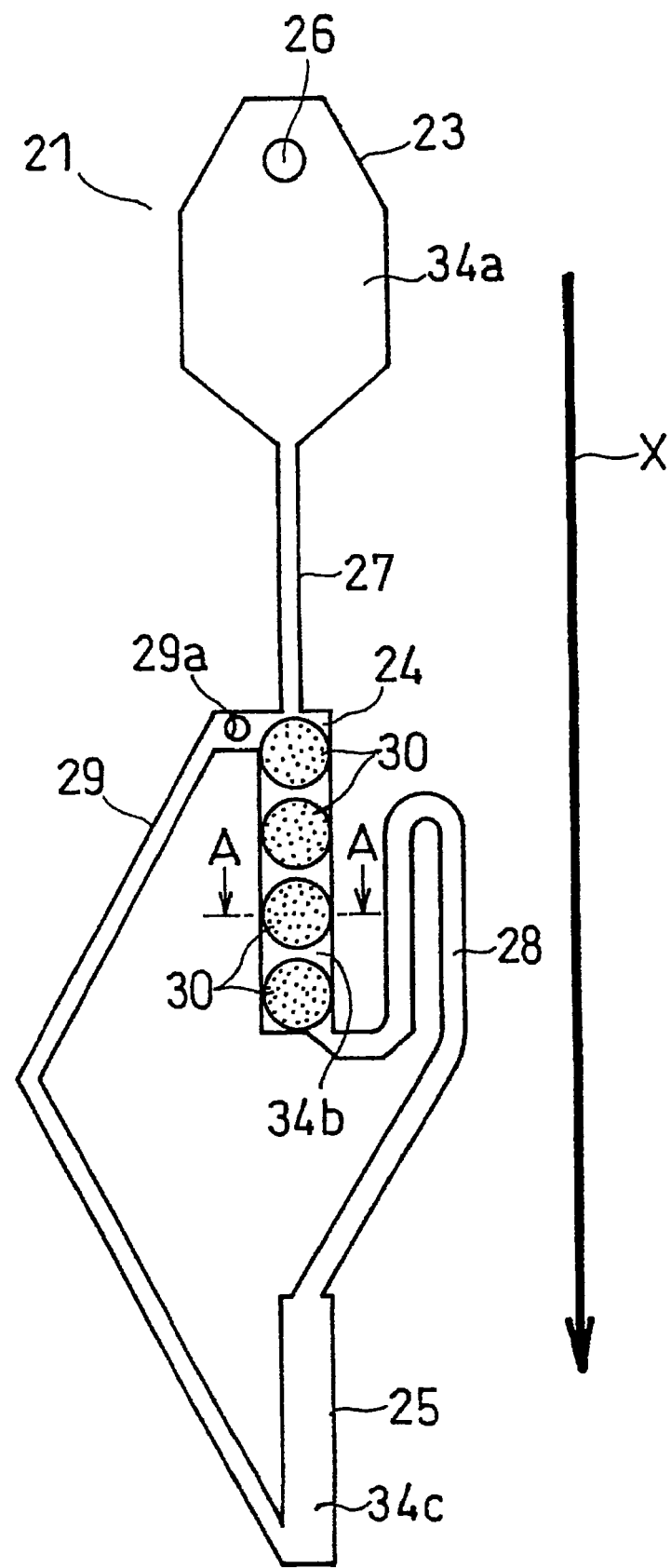
FIG. 2 An enlarged schematic view of an embodiment of a sample mixing unit in a sample-liquid analysis disc of the present invention, in the direction of normal to the disc main surface.

Next, as an embodiment of the present invention, a case using a substantially semi-spherical solid reagent is described by referring to FIGs. FIG. 2 is an enlarged schematic view of the sample mixing unit 21 in Embodiment 1 of the present invention, in the direction of normal to the main surface of the disc main body 20. The sample mixing unit 21 includes a liquid sample reserve unit 23, a reagent chamber 24, and a measurement chamber 25. The liquid sample reserve unit 23 includes a liquid sample supply-port 26.

In this embodiment, the reagent chamber 24 is configured to dispose solid reagents 30 in the direction substantially parallel to the diameter of the disc main body 20. The liquid sample reserve unit 23 is connected to the reagent chamber 24 via a first flow path 27. The width of the first flow path 27 is preferably, for example, 0.2 to 1.0 mm, since the liquid sample can be supplied further reliably, and the liquid sample backflow from the reagent chamber 24 to the liquid sample reserve unit 23 can be curbed. The length of the first flow path 27 may be for example 5 to 10 mm. The form of the reagent chamber 24 in this embodiment is substantially rectangular having a long side and a short side, when seen in the direction of normal to the main surface of the disc main body 20. The long side is arranged to be substantially parallel to the disc diameter (direction of centrifugal force A). In this way, the liquid sample flows in the reagent chamber 24 from the first flow path 27 further reliably.

The length of the long side of the above substantial rectangle may be the length that enables disposing a plurality of solid reagents 30. For example, when a number n (n≧2) of the solid reagent 30 with radius $R_0$ is to be disposed, a length larger than $2R_0 \times n$ is sufficient for the long side. Particularly, the length of the long side substantially equal to $2R_0 \times n$ is preferable, because the solid reagent 30 can be brought into close contact with the walls of the reagent chamber 24.

The length of the short side is not particularly limited, as long as the solid reagent 30 can be disposed inside. The length of the short side may be for example 0.8 to 2.0 mm, and preferably substantially equal to the diameter of the solid reagent 30 to be mentioned later. With the length of the short side substantially equal to the diameter of the solid reagent 30, the solid reagent 30 can be brought into close contact with the walls of the reagent chamber 24. In this way, capillarity is allowed to work further reliably, for example between the reagent chamber 24 and the solid reagent 30. At this time, the liquid sample flowed into the reagent chamber 24 dissolves reliably the portion of the solid reagent 30 contacting the walls of the reagent chamber 24. With a second flow path 28 having a bent structure to be mentioned later, the liquid sample stays in the reagent chamber 24 at the side closer to the rim of the disc main surface, without flowing into the measurement chamber 25. Since the portion of the solid reagent 30 that is in contact with the reagent chamber 24 is dissolved, with the centrifugal force, it makes contact with the liquid sample that is staying at the side closer to the rim of the disc and will be dissolved.

In the reagent chamber 24, for example, four substantially semi-spherical solid reagents 30 are disposed. The diameter of the solid reagent 30 is preferably for example 0.7 to 2.0 mm. The volume of the solid reagent 30 is 0.1 μl to 2.0 μl. It is preferable in that the formation of the solid reagent 30 becomes easier, and the solid reagent 30 is easily disposed in the reagent chamber 24. The reagent chamber 24 is configured so that the liquid sample is supplied from the liquid sample reserve unit 23 via the first flow path 27, based on centrifugal force A caused by the spinning of the disc main body 20, and capillarity caused in the first flow path 27.

The measurement chamber 25 is connected to the reagent chamber 24 via the second flow path 28. The second flow path 28 preferably is bent. In this way, the liquid sample stays in the reagent chamber 24 at the side closer to the rim of the disc main surface. The width of the second flow path 28 is preferably for example 0.2 to 1.0 mm. In this way, the sample mixture liquid can be supplied to the measurement chamber 25 further reliably, and also the backflow of the sample mixture liquid from the measurement chamber 25 to the reagent chamber 24 can be curbed. To the measurement chamber 25, the sample mixture liquid containing the liquid sample and the solid reagent 30 mixed in the reagent chamber 24 is supplied based on the centrifugal force caused by the spinning of the disc main body 20 and the capillarity that works on the second flow path 28. In the measurement chamber 25, chemical reaction of the sample mixture liquid is detected for example by an optical detection unit (not shown).

The measurement chamber 25 is also connected to the reagent chamber 24 via a third flow path 29. The third flow path 29 includes a hole 29a for a smooth distribution of the liquid sample and the sample mixture liquid.

The reagent forming the solid reagent 30 may be selected as appropriate depending on the kinds of the liquid sample to be measured, and the kinds of measurement, within the scope in which the present invention can be embodied. For example, when measuring a triglyceride concentration in plasma contained in blood, for example, at least one of the following may be used: cyclohexylaminoethanesulfonate (CHES), diaphorase, tetrazolium salt (WST-9), nicotinamide adenine dinucleotide (NAD), lipoprotein lipase, and glycerol dehydrogenase. The solid reagent 30 may contain any of the above reagents singly. When the solid reagent 30 containing a plurality of reagents has no problem in terms of storage characteristics, a solid reagent 30 containing a plurality of reagents may be used as well.

Figure 3:
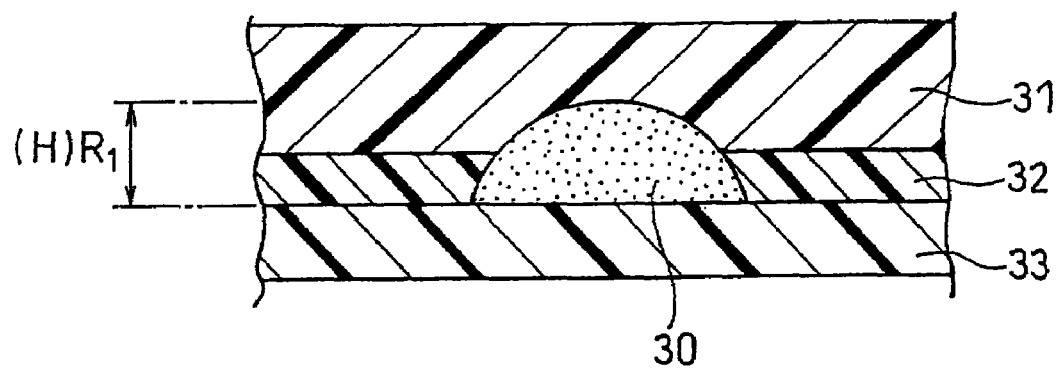
FIG. 3 A cross section of a relevant part of a reagent chamber in an embodiment of the present invention (cross section taken along the lines A-A in FIG. 2).

The disc main body 20 is configured with an upper base board (31 in FIG. 3, to be mentioned later), a spacer (FIG. 3, 32) and a lower base board (FIG. 3, 33). When the disc main body 20 includes the above-mentioned sample mixing unit 21 in the disc, the liquid sample reserve unit 23, the reagent chamber 24, and the measurement chamber 25 are formed by a space unit 34a, a space unit 34b, and a space unit 34c, respectively. The space units 34a, 34b, and 34c are formed by an upper base board 31, a spacer 32, and a lower base board 33.

Figure 4:
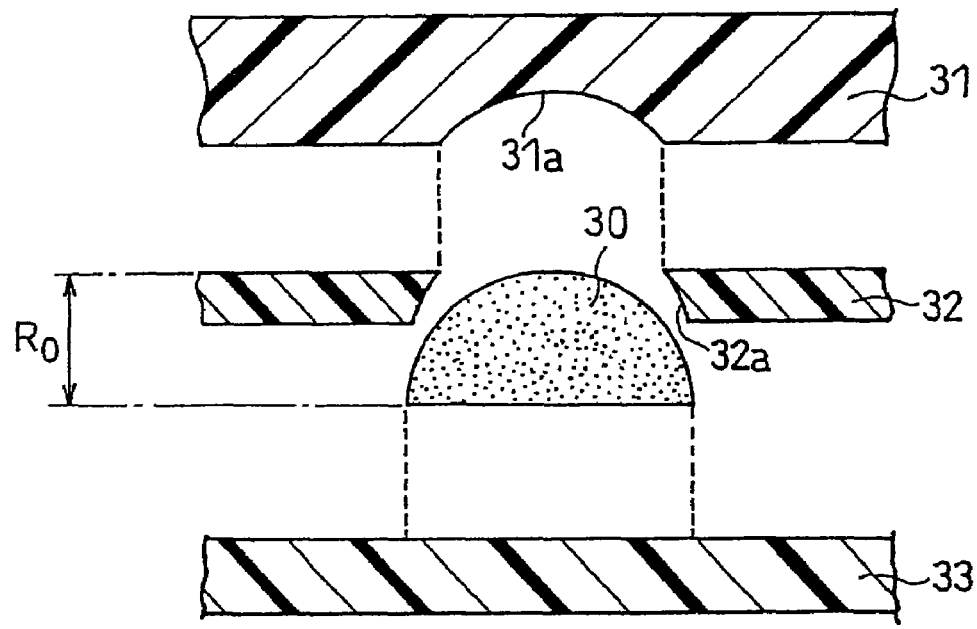
FIG. 4 A schematic diagram of a relevant part of a reagent chamber in one embodiment of the present invention, exploded in the direction of normal to the disc main surface.

FIG. 3 is a cross section of a relevant part of the reagent chamber 24 (cross section along the lines A-A in FIG. 2). FIG. 4 is a diagram of a relevant part of the reagent chamber 24 shown in FIG. 3, exploded in the direction of normal to the main surface of the disc main body 20. In FIG. 3 and FIG. 4, the upper base board 31 has a concave portion 31a, which forms an upper face and a portion of the side walls of the reagent chamber 24. For the upper base board 31, for example, a board including polycarbonate and having a thickness of 0.5 to 1 mm may be used. Preferably, the radius of curvature of the concave portion 31a is substantially the same as the form of the solid reagent 30. In this way, the solid reagent 30 is fixed further reliably by the reagent chamber 24, so that the deformation and damage to the solid reagent 30 can be curbed. The radius of curvature may be for example, 0.4 to 1.0 mm.

The spacer 32 includes a cutaway portion 32a corresponding to a portion of the side walls of the reagent chamber 24. For the spacer 32, for example, a board including polyethylene terephthalate and having a thickness of 50 to 200 μm may be used.

The lower base board 33 forms a bottom face of the reagent chamber 24. For the lower base board 33, for example, a board including polycarbonate and having a thickness of 0.5 to 5.0 mm may be used.

Although height H (a length of a side substantially parallel to the direction of normal to the disc main surface) of the reagent chamber 24 is not particularly limited as long as the solid reagent 30 (radius $R_0$) can be disposed inside, preferably, it is substantially equal to the height of the solid reagent 30 (radius $R_0$), or smaller than $R_0$. Particularly, height H of the reagent chamber 24 and radius $R_0$ of the solid reagent 30 preferably satisfy the relation formula $0.7R_0 \leq H \leq R_0$.

With height H of the reagent chamber 24 smaller than the radius $R_0$ of the solid reagent 30, when forming the reagent chamber 24, the solid reagent 30 is pressed by the inner wall of the reagent chamber 24, and height $R_0$ of the solid reagent 30 becomes $R_1$. In this way, the solid reagent 30 is fixed in the reagent chamber 24. At that time, $R_1$ is substantially equal to height H of the reagent chamber 24.

When height H of the reagent chamber 24 is substantially equal to radius $R_0$ of the solid reagent 30, the solid reagent 30 is preferably formed to closely contact the concave portion 31a, the cutaway portion 32a, and the lower base board 33. In this way, the solid reagent 30 is fixed in the reagent chamber 24, and chipping and cracking are hardly caused.

Next, an example of the configuration of the disc main body 20 is described. For the upper base board 31 and the lower base board 33, for example, a polycarbonate-made plate may be used. For the upper base board 31, for example, a plate with a thickness of 0.6 mm is used. For the lower base board 33, for example, a plate with a thickness of 0.6 mm is used. A spacer 32 is interposed between the upper base board 31 and the lower base board 33. For the spacer 32, for example, a polyethylene terephthalate-made plate may be used. The spacer 32 has a thickness of for example 100 μm. On both faces of the spacer 32, an adhesive is applied.

On one face of the upper base board 31, the liquid sample reserve unit 23, the reagent chamber 24, the measurement chamber 25, the first flow path 27, the second flow path 28, and the third flow path 29 are partially formed. The concave portion 31a forming the reagent chamber is for example a curved face having a radius of curvature of 0.75 mm, and a size of a direction substantially parallel to the direction of normal to the main surface of the disc main body 20 is for example 0.6 mm.

At the portion of the lower base board 33 where the reagent chamber 24 is formed, for example, four solid reagents 30 are disposed so that the spherical face of the solid reagent 30 and the concave portion 31a are brought in contact with each other. Each of the solid reagents 30 are arranged so that they are in close contact with each other. For the solid reagent 30, for example, a substantially semi-spherical reagent with a volume of 1.0 μl is used. The diameter of the solid reagent 30 is about 1.56 mm, in the case of a substantially semi-spherical reagent with a volume of 1.0 μl. The size of the liquid sample reserve unit 23 is set so that a liquid sample with at least a volume of the solid reagent 30, that is, a volume of 1.0 μl, is placed. For example, the size may be a height of 0.3 mm, and a bottom face of 3.5 $mm^2$. Such a size renders the volume 1.05 μl, so the conditions are met. However, before supplied from the liquid sample reserve unit 23 to the reagent chamber 24 via the first flow path 27, it is adsorbed and remained at the inner walls of the liquid sample reserve unit 23 and the first flow path 27. That is, the amount of the liquid sample to be supplied to the reagent chamber 24 is smaller than the amount of the liquid sample to be supplied to reserve unit 23. Thus, the volumetric capacity of the liquid sample reserve unit 23 is preferably larger than 1.0 μl. For example, with a height of 0.3 mm, and a bottom face area of 4 $mm^2$ (a volume of 1.2 μl), a sufficient amount of the liquid sample can be supplied to the reagent chamber 24.

The above-mentioned upper base board 31, and the lower base board 33 are laminated with a spacer 32 having a thickness of 100 μm interposed therebetween. In this way, the liquid sample reserve unit 23, the reagent chamber 24, the measurement chamber 25, the first flow path 27, the second flow path 28, and the third flow path 29 are formed. The solid reagent 30 is fixed in the reagent chamber 24 at this time. The reagent chamber 24 is substantially rectangular having a long side and a short side, seeing in the direction of normal to the main surface of the disc main body 20. The long side is arranged so that it is substantially parallel to the radial direction of the disc main body 20. The length of the long side is for example 7 mm, and the length of the short side is for example 1.56 mm. By laminating the upper base board 31, the spacer 32, and the lower base board 33, height H of the reagent chamber 24 (space unit 34b) becomes about 0.7 mm.

The method for manufacturing the solid reagent 30 is not particularly limited, as long as the method achieves obtaining the solid reagent 30 to be disposed in the reagent chamber 24 in an amount necessary for the reaction when being dissolved in the liquid sample. For example, it can be obtained by filling the powder of the reagent forming the solid reagent 30 in a mold having a predetermined form, and compressing. It can also be obtained by dropping an aqueous solution containing a reagent forming the solid reagent 30 on a base board, and freeze-drying while controlling to give an arbitrary diameter. In this case, a freeze-dry powder may be put into a mold having a predetermined form for the molding. A substantially semi-spherical solid reagent 30 may also be obtained by dropping an aqueous solution containing a reagent forming the solid reagent 30 on a base board with an appropriate degree of water-repellency, that is, a Teflon® plate, or a resin or metal plate treated with a water-repellent of fluorine-type or silicon-type, and freeze-drying.

Particularly, the solid reagent formed of freeze-dried, granular reagent is preferable. The freeze-dried granules are preferably formed by dropping an aqueous solution containing a reagent forming the solid reagent. In this way, the surface area of the solid reagent can be controlled. Therefore, the solid reagent can be further made easier to be dissolved in the liquid sample. A smooth surface, uniform, and homogenous solid reagent can also be made.

In the following, a preferable embodiment for obtaining a preferable form of the solid reagent, i.e., freeze-dried granules, is described. A method for obtaining a solid reagent, i.e., freeze-dried granules, from an aqueous solution containing at least one reagent forming the solid reagent preferably includes the steps of: (A) dropping an aqueous solution containing a reagent forming a solid reagent on a base board having a surface treated with a water-repellent; (B) freezing the aqueous solution containing the reagent forming the solid reagent dropped on the base board; and (C) heating the aqueous solution containing the reagent forming the solid reagent under a reduced-pressure environment, to sublimate water molecules for drying, thereby obtaining a solid reagent of freeze-dried granules.

In this embodiment, the aqueous solution containing a reagent forming the solid reagent is dropped on a base board surface treated with a water-repellent with a dispenser or a pipet, to obtain uniformly-sized droplets. The droplets are frozen, and further freeze-dried under a reduced pressure. The surface treated with the water-repellent has a concave portion having a form of a portion of a sphere, and by carrying out the above-mentioned steps (A) to (C) in the concave portion, the droplets of the reagent solution dropped on the base board are disposed at each of the concave portion. That is, the droplet of the uniformly-shaped reagent solution can be disposed on the base board. By freeze-drying the droplets, a plurality of the uniformly-shaped solid reagents are formed easily and thus preferable.

[Step (A)]

The concentration of the aqueous solution containing the reagent forming the solid reagent may be adjusted suitably within the range which enables obtaining freeze-dried granules that will not damage the effects of the present invention. For example, when WST-9 (molecular weight 629.6) is used, an aqueous solution of about 100 mM is preferably used.

The contact angle of the droplets of the aqueous solution containing a reagent forming the solid reagent on the base board is preferably 75° or more, so that the spread of the dropped reagent solution on the base board surface before the freezing can be curbed. In this way, a substantially semi-spherical, frozen solid containing the reagent solution can be obtained. By freeze-drying this, a substantially semi-spherical solid reagent can be easily obtained. The contact angle of 150° or more is further preferable, since the form of the solid reagent can be controlled further easily. For the base board, for example, a polytetrafluoroethylene (PTFE)-made base board having a water-repellent surface may be used. Also, the surface of a hydrophilic base board may be treated with a water-repellent to give water repellency. For the water-repellent, a coating agent which is highly effective in giving water-repellency, and which is not denatured or dissolved by the aqueous solution containing a reagent forming the solid reagent is preferably used.

That is, the surface treated with a water-repellent is preferably formed with a fluorocarbon resin coating. The surface treated with a water-repellent may also be formed with a silicone resin-type coating. Some of these coating agents have a contact angle of 100° or more, and even a contact angle of 150° or more to pure water. Further, some of these coating agents have a significantly large contact angle even to an aqueous solution containing a surfactant. With a base board having a surface treated with such a coating agent, even an aqueous solution containing a surfactant does not easily spread on the base board.

However, with an excessively water-repellent base board, the aqueous solution containing a reagent forming the solid reagent cannot be adsorbed on the base board, and the dropping from the dispenser or pipet becomes difficult. For curbing such, for example, a tip of the dispenser or pipet may also be treated to give water-repellency. The droplets may be blown off to be hurled against the base board by shortening the time of discharging from the dispenser or pipet, so that the droplets can be attached to the base board.

Further, to attach the droplets to the base board reliably and easily, as the base board to be treated and given water repellency, preferably, a hydrophilic material is selected, and the coating agent is removed partly from the surface treated with a water-repellent. In this way, droplet adsorption may be induced. The area where the coating agent is to be removed is preferably larger to the extent that the adsorption of the droplet to the base board is facilitated more than the adsorption of the droplet to the tip of the dispenser and the pipet. That is, the size is preferably set to the extent that the outer side of the circle region created at the contact portion of the dropped droplet to the base board is in contact with the coating agent. In this way, the base board can keep the contact angle similar to the case when the coating agent is not removed for the droplets. For example, the diameter of the area to be removed is preferably 0.3 to 0.6 mm, in the case of a droplet of the reagent solution in an amount of 1 µl. For example, when the diameter is 0.3 mm, the contact angle between the reagent solution and the base board is about 150°. When the diameter is 0.6 mm, the droplet of the reagent solution is for example substantially semi-spherical. When extremely large, adsorption becomes extremely high, and therefore the contact angle between the droplet and the base board becomes smaller. Thus, as a result, it becomes difficult to obtain spherical or semi-spherical freeze-dried granules.

For example, when a coating agent having a contact angle of 150° is used, the dropped droplets become substantially spherical. At this time, the diameter of the portion contacting the base board becomes about the half of the diameter of the droplet. This is easily derivable from geometric analysis.

At the surface of the above-mentioned base board, the portion not treated to give water-repellency is preferably surrounded by the portion treated to give water-repellency. In this way, the shape of the reagent solution droplets can be easily controlled. By dropping the reagent solution at such a portion of the base board where the water-repellent treatment is not given, based on the amount of the reagent solution drops and the area of the portion not treated with the water-repellent, the contact angle becomes smaller than the contact angle between the base board treated with the water-repellent and the reagent solution, and a larger droplet can be freely obtained.

Such a base board can be obtained, for example, as in below. First, a water-repellent is applied to an ordinary base board having a water-repellent (or hydrophilic) surface, such as a polyethylene terephthalate (PET)-made base board. Afterwards, a portion of the applied water-repellent is scraped off, to expose the surface of the base board.

In this way, when an aqueous solution containing a reagent forming the solid reagent is dropped on the base board surface with a pipet, the aqueous solution is easily transferred from the tip of the pipet to the base board surface. That is, by forming a portion with a high water-repellency and a portion with a low water-repellency, anchor effect can be imparted between the portion with a high water-repellency and the portion with a low water-repellency. Thus, the droplets can be held at the base board surface further reliably.

[Step (B)]

Following the above step (A), the aqueous solution containing the reagent forming the solid reagent dropped on the base board mentioned above is frozen. Afterwards, before or after freeze-drying (step (C)), the frozen aqueous solution is preferably removed from the base board. In this way, without damaging the frozen material of the reagent solution or solid reagent at the time of removal, a frozen material of the reagent solution or a solid reagent having a predetermined form can be obtained.

[Step (C)]

The conditions for the freeze-drying can be suitably adjusted as long as the effects of the present invention are not damaged. For example, adjustment can be made as in below. For example, under an environment of an atmospheric pressure of 613 Pa (4.6 Torr), water is boiled at 0° C. That is, in the case of pure water, at 0° C. and an atmospheric pressure of 4.6 Torr, sublimation occurs. With a further reduced atmospheric pressure, the temperature for the sublimation occurrence also decreases. For example, when the temperature is decreased to minus 40° C., the sublimation occurs at an atmospheric pressure of 0.1 Torr or less. The sublimation is further facilitated when the atmospheric pressure is set to 0.1 Torr, and the temperature is gradually increased from minus 40° C. Only the moisture content is thus sublimated from the frozen aqueous solution containing the reagent forming the solid reagent while in frozen state, and finally the water content is lost almost completely. In this way, only the reagent forming the solid reagent is solidified and held on the base board.

However, in reality, when sublimation occurs, water vapor remains in the proximity of the solution containing the frozen reagent forming the solid reagent. The atmospheric pressure (vapor pressure) partially increases in the proximity of such an area in this way, which decreases the efficiency of the sublimation. Thus, to quickly advance the sublimation substantially, the following are important: (1) increase temperature to advance the sublimation even in a further high atmospheric pressure, and (2) quickly remove the water vapor surrounding the aqueous solution containing a reagent forming the solid reagent to curb the increase in the atmospheric pressure.

For the purpose of the (1) above, the temperature is increased gradually so that the temperature reaches about 20 to 30° C. finally. Since the latent heat is lost at the time of the sublimation, even with the temperature increase at the outer side, when the temperature increase is not so rapid, the frozen aqueous solution containing a reagent forming the solid reagent is not melted.

For the purpose of (2) in the above, a "trap device" is preferably provided at the freeze-drying device. The trap device is set to have a temperature further lower than the lowest temperature in the space for the freeze-drying, and has a function of freezing and collecting the surrounding water vapor. The trap device and the space for the freeze-drying are communicating, so that gases can be passed between them. The trap device collects water vapor, and the vapor pressure decreases, thus the vapor pressure in the proximity of the frozen aqueous solution containing a reagent forming the solid reagent further decreases.

Freeze-drying can be carried out with a freezing temperature of below 0° C., and an atmospheric pressure of below 4.6 Torr. However, sometimes there remains an area partially unfrozen even with about minus 20° C., due to a molar freezing point depression of the aqueous solution containing a reagent forming the solid reagent. Also, since when the initial atmospheric pressure is set to 4.6 Torr, even a small degree of sublimation, the atmospheric pressure exceeds the point where water vapor sublimates, which damages the efficiency, thus a further low pressure is preferable.

Thus, in this embodiment, the freeze-drying is started from minus 40° C. or less and an atmospheric pressure of 0.1 Torr or less, and the temperature is gradually increased while keeping the atmospheric pressure as it is. The inventors of the present invention confirmed based on examination that when the volume of the aqueous solution containing a reagent forming the solid reagent is 100 µl or less, homogenous freeze-dried granules can be obtained by increasing the temperature to room temperatures (for example, to 25 to 40° C., further to 25 to 30° C.) taking four or more hours while keeping the atmospheric pressure to 0.1 Torr or less, and then drying the aqueous solution for about 4 hours or more. The temperature after the heating is preferably around room temperature (20 to 40° C.). The temperature too low is not preferable, because it takes too much time for the sublimation of water content. On the other hand, the temperature too high is not preferable because the freeze-dried granules may be denatured.

In this embodiment, the amount of the aqueous solution containing a reagent forming the solid reagent is preferably 10 µl or less. In this way, the heating time and the drying time at the temperature after heating can be further shortened. With an excessively rapid heating from the initial temperature, the temperature exceeds the melting point while leaving water content, and frozen state may be lost. On the other hand, an excessively long period for leaving after the heating is not preferable, since the remained freeze-dried granules may be denatured.

The manufacturing method in this embodiment is preferably used when the volume of the droplet of the aqueous solution containing the reagent forming the solid reagent is about 0.1 to 10 µl. With the volume of the droplet within this range, handling after the freeze-drying becomes easier, and excellent substantially spherical droplets can be obtained.

The aqueous solution containing a reagent forming the solid reagent is preferably dropped on the base board which is cooled to the melting point or below of the reagent solution, not dropping the aqueous solution containing a reagent forming the solid reagent on the base board and then cooling the base board. That is, before step (A), a step for cooling the base board to the freezing point or below of the aqueous solution is preferably included. In this way, the portion making contact with the base board is frozen almost in a second, and then the droplet surface is frozen. Thus, without the spread of the aqueous solution on the base board, excellent spherical frozen particles can be obtained. When freeze-dried under such conditions, excellent spherical freeze-dried particles can be obtained.

When this method is used, further larger droplets can be obtained compared with the case when the freezing is carried out by cooling the base board and the surrounding of the droplet after the dropping. This is because the freezing form of the droplets can be controlled, by adjusting the amount of the solution to be discharged from the dispenser and pulling up the tip of the dispenser to allow the entire droplet to be frozen, at the time when a portion of the droplet is allowed to contact the base board and the freezing is carried out.

However, the freezing speed of the solution is affected by the temperature of the base board surface, the temperature of the droplet, and the temperature and humidity surrounding the base board and the droplet, and the speed varies even the dropping is carried out under the same conditions. Therefore, preferably, such a method is applied by making a limitation to a liquid with a relatively low effect of the coating agent.

This method can also be applied without the coating agent to obtain the spherical freeze-dried granules, but not preferable because cracks and chipping of the freeze-dried granules are easily caused in the proximity of the area contacting the base board when the freeze-dried granules are removed from the base board after the freeze-drying, and also the freeze-dried granules easily remain on the base board.

To obtain the freeze-dried granules by such a method, not only the reagent forming the solid reagent, but as necessary, an additive for keeping the external configuration of the freeze-dried granules may be necessary.

The kind and amount of the additive depend on its application but those skilled in the art can suitably make selections. For example, saccharides such sucrose is suitable for such application.

The composition and the concentration of the aqueous solution containing a reagent forming the solid reagent heavily depend on the properties of the each solid reagent. Depending upon the combination of the reagents, even the combination of the reagent is necessary for the entire reaction, when freeze-dried as a mixed solution with the above-mentioned method, sometimes it quickly deliquesces when brought into contact with about the indoor humidity. In this case, the deliquescence can be avoided by selecting a reagent group of a preferable combination of two or more reagents from the reagents necessary for the reaction, to form the freeze-dried granules. In the case when the combination of the reagents necessary for the entire reaction is extremely unstable under a state of mixed solution as well, similar measures can be taken, and by taking such measures, storage stability of the solid reagent improves.

Next, a method for analyzing a sample mixture liquid by using the above-mentioned sample-liquid analysis disc is described.

First, a mechanism by which the liquid sample and the solid reagent 30 are mixed in the reagent chamber 24 is described.

In view of the solubility of the solid reagent 30, and stability of the reagent solution used when manufacturing the solid reagent 30, the reagent density of the solid reagent 30 (the reagent amount per unit volume) is preferably substantially the same with the reagent concentration in the reagent solution, or less. Since some reagents are required to be formed as separate solid reagent 30 and mixed at the time of reaction to avoid a decrease in stability due to mixing of the solid reagent 30, a plurality of the solid reagent 30 are disposed in a single reagent chamber 24.

Then, a liquid sample corresponding to the volume of one solid reagent 30 is supplied from a supply port 26 to the liquid sample reserve unit 23. By spinning the disc main body 20 with a motor (not shown), with centrifugal force caused by the spinning of the disc main body 20 and the capillarity in the first flow path 27, the liquid sample in the liquid sample reserve unit 23 flows into the reagent chamber 24. At this time, the liquid sample is brought into contact with the surrounding of the solid reagent 30 reliably, dissolving at least the rim area of the solid reagent 30.

At this time, since the amount of the liquid sample only corresponds to the volume of one solid reagent 30, even though the liquid sample is entirely flowed into the reagent chamber 24, only the solid reagent disposed at the outermost position in centrifugal force direction X completely sunk among the solid reagents 30 disposed in series in centrifugal force direction X.

Thus, the solid reagent 30 not dissolved when the liquid sample flowed in remains undissolved when left as it is. Since the solid reagent 30 is disposed to fill the reagent chamber 24, the liquid sample stays at the side closer to the rim of the disc main body 20. With dissolution of the rim of the solid reagent 30 and the action of the centrifugal force, the solid reagents 30 remained undissolved are sunk in the liquid sample stayed at the side closer to the rim of the disc main body 20, and dissolved in the liquid sample.

At this time, a portion of the solid reagent 30, gelled between the liquid level of the mixed sample and the solid reagent 30 remained undissolved, remains at the inner wall of the reagent chamber 24. Then, the sample mixture liquid contained in the partially gelled solid reagent 30 reaches the portion having no contact with the liquid sample by capillarity, starting the dissolution of the solid reagent 30 remained undissolved. Further, the gelled solid reagents 30 also are gradually dissolved, and finally entirety of the solid reagents 30 is sunk in the liquid sample to be dissolved, thereby becoming a sample mixture liquid.

In this way, the time for dissolving the solid reagent in the liquid sample and for the reaction between them can be shortened. Thus, the chemical reaction of the sample-solution can be detected further accurately.

The sample mixture liquid is supplied to the measurement chamber 25 from the reagent chamber 24 via the second flow path 28 by the act of capillarity and centrifugal force. The chemical reaction of the sample mixture liquid supplied to the measurement chamber 25 is preferably detected optically. For example, by detecting the amount of the transmitted light in the sample mixture liquid or the changes in absorbance, the chemical reaction of the sample mixture liquid can be detected further accurately.

Next, as a specific analysis method, described is a case where a concentration of triglyceride (neutral fat, hereinafter referred to as TG) in plasma is measured.

Used for the solid reagent 30 was freeze-dried granules obtained by freeze-drying a solution of reagent group necessary for the reaction in water or a pH buffer solution. For the reagent used for detecting the TG, when all the reagents are made into one solid reagent 30, denaturing may occur based on the interaction between the reagents. Thus, in this embodiment, reagents are divided into four groups, and the solid reagents 30 containing respective reagents are used. The solid reagents 30 of four types are disposed in one reagent chamber 24.

As mentioned above, the sample mixture liquid mixed in the reagent chamber 24 is supplied to the measurement chamber 25. Then, in the measurement chamber 25, changes in absorbance of a specific wavelength of pigment contained in the solid reagent 30, that is dependent on the chemical reaction of TG, are detected.

Therefore, as described above, the bottom face and the upper face of the measurement chamber 25 are required to be smooth and substantially transparent optically to wavelength. The depth of the measurement chamber 25 corresponds to light path length when measuring the transmitted light, and therefore the amount or absorbance of the transmitted light in the sample mixture liquid is set appropriately to be suitable. In the case of the solid reagent 30 to be mentioned later, for example, 200 μm is preferable.

To measure the TG concentration in plasma, the reaction mechanism below is used.

(1) TG→glycerol (enzyme: lipoprotein lipase)

(2) glycerol+NAD→dihydroxyacetone+NADH (enzyme: glycerol dehydrogenase)

(3) NADH+WST-9→NAD+formazan (enzyme: diaphorase)

By measuring the amount of the changes in the absorbance (of the transmitted light in a wavelength of 650 nm due to the formazan generation in the above-mentioned formula (3)) corresponding to the concentration, the concentration of glycerol generated from TG is calculated.

Plasma contains a small amount of glycerol. Therefore, when the TG concentration is to be measured further accurately, it is desirable to measure the glycerol concentration by using a measurement system with only reaction formulae (2) and (3), and carrying out counterbalancing.

For the reaction, a pH buffering agent called CHES is used as a buffering agent for adjusting pH. In the above-mentioned formulae (2) and (3), the abbreviation NAD stands for nicotinamide adenine dinucleotide, i.e., an oxidized form of nicotinamide adenine dinucleotide, and NADH stands for the same of a reduced form. WST-9 is an acronym for "water-soluble tetrazolium-9" and is one of the tetrazolium salts that can be obtained from Dojindo Laboratories. Diaphorase is an enzyme that catalyzes the oxidation reaction of NADH to NAD, and the conjugated reduction reaction.

For the solid reagent 30, four kinds of reagents are used: CHES, i.e., a pH buffering agent, diaphorase, a mixture of WST-9 and NAD, and a mixture of lipoprotein lipase and glycerol dehydrogenase.

For the each solid reagent 30, for example, a substantially dome-shaped with a volume of 1 μl is used. The four solid reagents 30 are disposed in the reagent chamber 24 in series so that the four solid reagents 30 are brought into contact.

In the reagent chamber 24, the solid reagents 30 are preferably disposed from the center of the disc main body 20 in the above-mentioned order. By disposing the solid reagents 30 in such an order considering the differences in solubility, the solid reagents 30 can be dissolved in the liquid sample further reliably.

To the liquid sample reserve unit 23 in the disc main body 20 including the above-mentioned solid reagents 30, standard serum or a liquid sample of standard serum diluted in a normal saline solution is supplied. Afterwards, disc is spun and the measurement of the absorbance by the sample mixture liquid was carried out with the measurement device. As a result, the solid reagents 30 are dissolved completely, and the changes in the absorbance that are dependent upon the TG concentration of the sample mixture liquid were observed. FIG. 5 shows the results.

Embodiment 2

Figure 6:
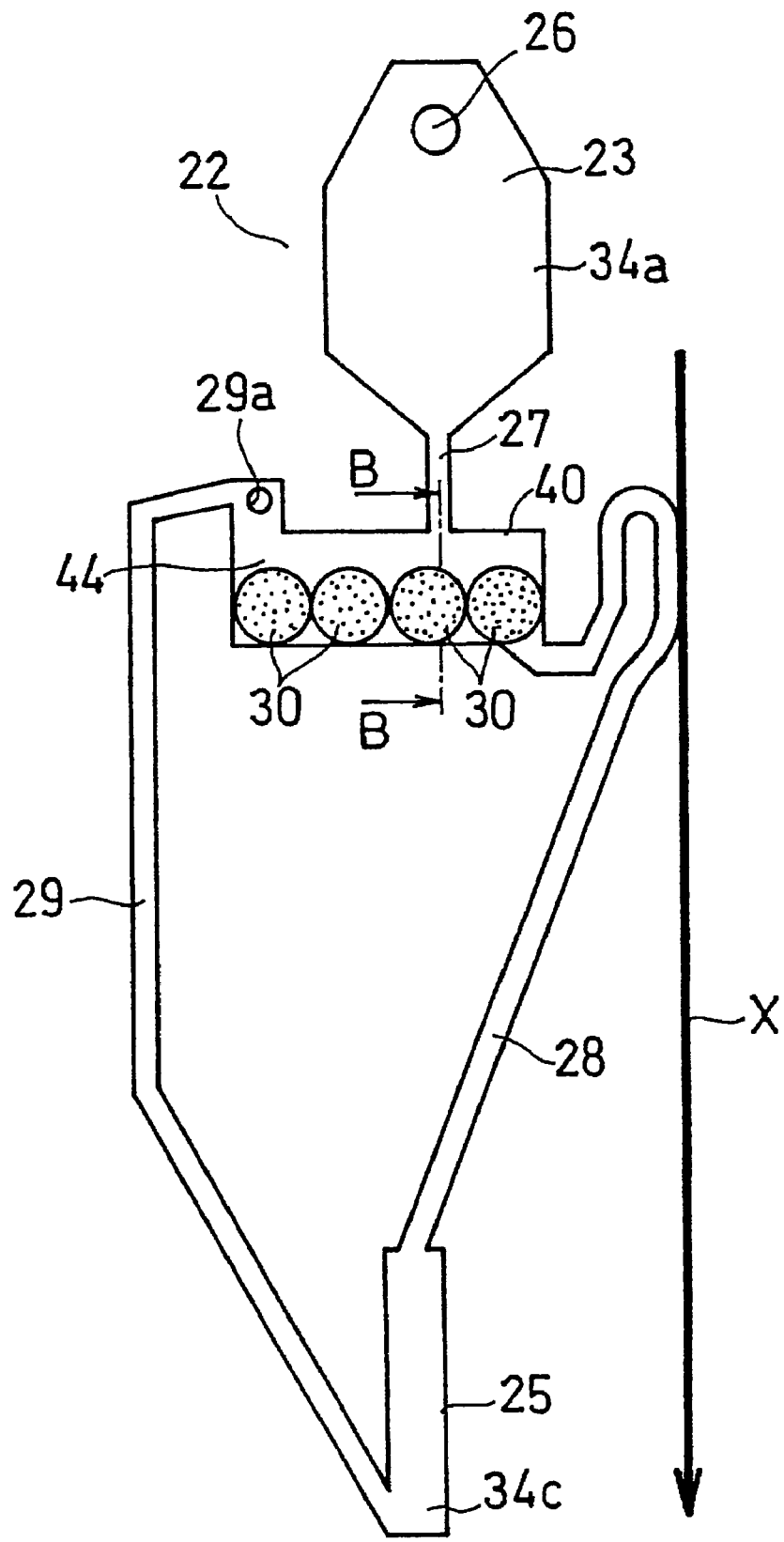
FIG. 6 An enlarged schematic view of a sample mixing unit of a sample-liquid analysis disc in another embodiment of the present invention, in the direction of normal to the disc main surface.

In this embodiment, the form of the sample mixing unit, especially the form of the reagent chamber is different in the sample-liquid analysis disc. FIG. 6 is an enlarged schematic view of a sample mixing unit 22 in Embodiment 2 of the present invention, in the direction of normal to the main surface of a disc main body 20. The same reference numbers are used for the elements similar to those in Embodiment 1, and descriptions are omitted.

In this embodiment, the reagent chamber 40 is formed so that the solid reagents 30 are disposed in the direction substantially perpendicular to the radial direction of the disc main body 20.

Figure 7:
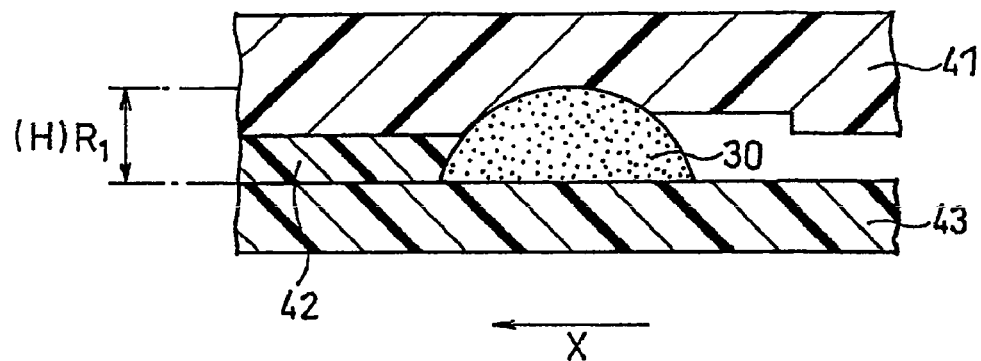
FIG. 7 A cross section of a relevant part of a reagent chamber in another embodiment of the present invention (cross section taken along the lines B-B in FIG. 6).
Figure 8:
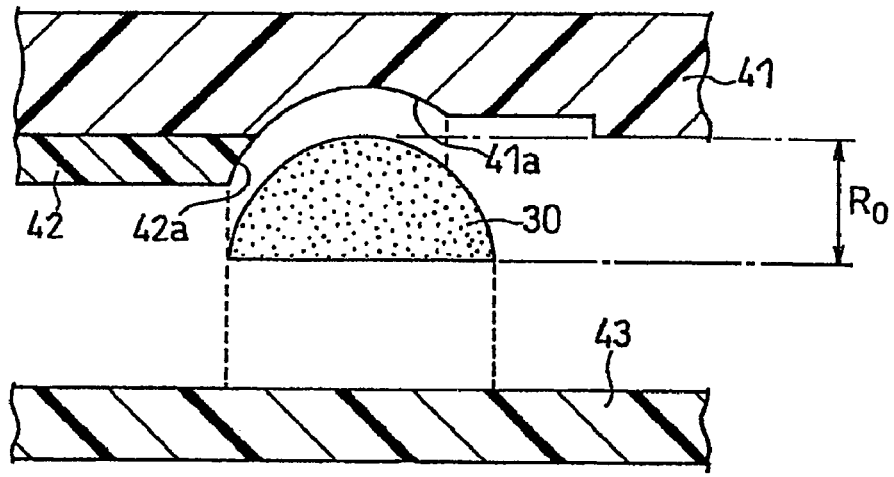
FIG. 8 A schematic diagram of a relevant part of a reagent chamber in another embodiment of the present invention, exploded in the direction of normal to the disc main surface.
Figure 9:
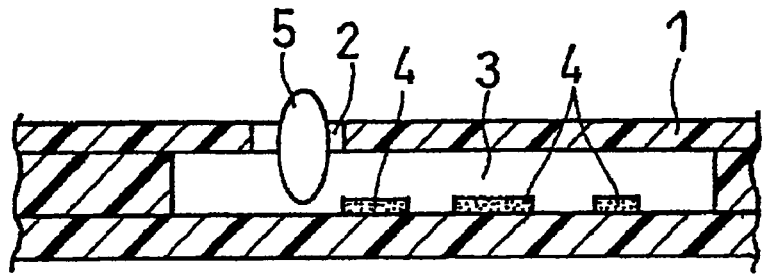
FIG. 9 A schematic cross section illustrating an example of a chamber in an analysis disc used in a conventional sample mixture liquid analysis device.

FIG. 7 is a cross section of a relevant part of a reagent chamber 40 (cross sectional view along the lines B-B in FIG. 6). FIG. 8 is a view of a relevant part of the reagent chamber 40 shown in FIG. 7, exploded in the direction of normal to the main surface of a disc main body 20. As shown in FIG. 7, the reagent chamber 40 (space unit 44) is formed with the upper base board 41, the spacer 42, and the lower base board 43.

The upper base board 41 includes a concave portion 41a, which forms a portion of the inner wall (a portion of the upper face and the side wall) forming the space unit 44 of the reagent chamber 40. The spacer 42 includes a cutaway portion 42a, which forms a portion of the side wall of the reagent chamber 40. The lower base board 43 forms the bottom face of the reagent chamber 40. For the upper base board 41, the spacer 42, and the lower base board 43, the same materials as those used in Embodiment 1 may be used.

The reagent chamber 40 in this embodiment is substantially rectangular having a long side and a short side, viewing in the direction of normal to the main surface of the disc main body 20. The long side is arranged to be substantially perpendicular to the radial direction of the disc main body 20 (the direction of centrifugal force A).

The length of the long side of the above-mentioned substantially rectangle may be the length that allows the solid reagents 30 to be disposed in the reagent chamber 40. For example, when the solid reagent 30 with radius $R_0$ is to be disposed in number n, the length of the long side may be larger than $2R_0 \times n$. Particularly, with the length of the long side that is substantially equal to $2R_0 \times n$, the water level of the liquid sample in the radial direction can be made maximum within the possible range in this configuration, when the liquid sample flowed in stays at the rim side of the main surface of the disc main body 20. In this way, when the liquid sample is supplied into the reagent chamber 40, the area where the solid reagent 30 is sunk in the liquid sample can be made larger and therefore particularly preferable. The length of the short side of the reagent chamber 40 is not particularly limited, as long as the solid reagents 30 can be disposed inside. The length of the short side may be for example 2 to 10 mm.

The height of the reagent chamber 40 (length of the side substantially parallel to the direction of normal to the main surface of the disc main body 20) is not particularly limited as well, as long as the solid reagents 30 can be disposed inside, but preferably substantially equal to or smaller than the height of the solid reagent 30 (radius $R_0$). Particularly, height H of the reagent chamber 40 and the radius of the solid reagent 30 preferably satisfy the relation formula $0.7 \leq H \leq R_0$.

When height H of the reagent chamber 40 is smaller than height $R_0$ of the solid reagent 30, similarly to the case in Embodiment 1, the solid reagent 30 is pressed against the inner wall of the reagent chamber 40, thereby setting height $R_0$ of the solid reagent 30 as $R_1$. In this way, the solid reagent 30 is fixed in the reagent chamber 40. At this time, $R_1$ is substantially equal to height H of the reagent chamber 40.

When height H of the reagent chamber 40 is substantially equal to the radius $R_0$ of the solid reagent 30, the solid reagent 30 preferably has such a form that the solid reagent 30 is brought into close contact with the concave portion 41a, the cutaway portion 42a, and the lower base board 43. In this way, the solid reagents 30 are fixed in the reagent chamber 40, hardly causing chipping and cracks.

Next, a specific example of a configuration of the sample mixing unit 22 is described. On one side of the upper base board 41, the liquid sample reserve unit 23, the reagent chamber 40, the measurement chamber 25, the first flow path 27, the second flow path 28, and the third flow path 29 are partially formed. The concave portion 41a forming the reagent chamber 40, for example, is a curved face with a radius of curvature of 0.75 mm, and the size that is substantially parallel to the direction of normal to the main surface of the disc main body 20 is for example 0.6 mm.

In the lower base board 43, four solid reagents 30 are disposed at the position where the reagent chamber 40 is formed as in Embodiment 1. At this time, the four solid reagents 30 are disposed so that spherical face of the solid reagent 30 and the concave portion 41a are in contact with each other. The solid reagents 30 are disposed so that the solid reagents 30 are in close contact. In this way, capillarity works further reliably between the solid reagents 30 and the wall face of the reagent chamber 40. That is, since the sample solution penetrates between the wall face of the reagent chamber 40 and the solid reagents 30 reliably, the solid reagents 30 are dissolved further reliably.

In the upper face of the reagent chamber 40, the side near the center of the disc (where the solid reagents 30 are not brought into contact) may be flat. At this portion, a level difference may be provided to distinguish the level of the flowing portion from the liquid sample reserve unit 23, so the height is set to 200 μm. With the spacer 42 of 100 μm interposed, the upper base board 41 is laminated. In this way, the liquid sample reserve unit 23, the reagent chamber 40, the measurement chamber 25, the first flow path 27, the second flow path 28, and the third flow path 29 are formed. At this time, the solid reagents 30 are fixed in the reagent chamber 40. This reagent chamber 40 is substantially rectangular having a long side and a short side, viewing in the direction of normal to the main surface of the disc main body 20. The long side is arranged so that it is substantially perpendicular to the radial direction of the disc main body 20. The length of the long side is for example 6.25 mm, and the length of the short side is for example 3 mm. By laminating the upper base board 31, the spacer 32, and the lower base board 33, height H of the reagent chamber 40 (space unit 44) becomes about 0.7 mm. Other height is 0.3 mm.

Next, a method for analyzing a sample mixture liquid is described.

A liquid sample corresponding to the volume of one solid reagent 30 is supplied to the liquid sample reserve unit 23 from the liquid sample supply-port 26. By spinning the disc main body 20 with a motor (not shown), with the centrifugal force caused by the spinning of the disc main body 20 and the capillarity in the first flow path 27, the liquid sample in the liquid sample reserve unit 23 flows into the reagent chamber 40.

At this time, the portion of all the solid reagents 30 near the long side in the reagent chamber 40 sunk in the liquid sample reliably, and at least a portion of the solid reagents 30 are dissolved. As described in Embodiment 1, by setting the reagent concentration in the liquid reagent substantially the same level or less, even though all the liquid sample flowed into the reagent chamber 40 in the case when a plurality of the solid reagents 30 are disposed in one reagent chamber 40, right after the flowing of the liquid sample, the solid reagents 30 are not completely sunk in the liquid sample.

Therefore, the portion of the solid reagents 30 not dissolved when the liquid sample flowed in remains undissolved when left as is. As shown in FIG. 7, the solid reagents 30 are disposed to contact the concave portion 41a and a long side portion of the reagent chamber 40. When the liquid sample is supplied to the reagent chamber 40, first, a portion of the solid reagents 30 is dissolved in the liquid sample. Then, since the undissolved portion also is in contact with the liquid sample, with capillarity, the liquid sample penetrates the undissolved solid reagents 30. The portion of the undissolved solid reagent 30 is dissolved, and further, with the action of centrifugal force, the solid reagents 30 still remained undissolved are sunk in the liquid sample staying at the outer side of the reagent chamber 40 in the centrifugal force direction, and are dissolved in the liquid sample as a result. Then, all the solid reagents 30 are finally sunk and dissolved in the liquid sample.

The sample mixture liquid in which the solid reagent 30 and the liquid reagent are mixed is supplied from the third flow path 29 with centrifugal force and capillarity to the measurement chamber 25, and measured with optical means in the measurement chamber 25.

In the above embodiments, the measurement chamber 25 reserves the sample mixture liquid for the optical measurement, but by further connecting a reagent chamber to the reagent chamber 40, it can be used also for a measurement system which requires many solid reagents 30. The configuration of such a chamber may be suitably selected for an optimal embodiment according to the reagent arrangement of the measurement system.

By using the sample-liquid analysis disc in this embodiment, the TG concentration in plasma was measured under the same conditions as in Embodiment 1. As a result, the solid reagent 30 was dissolved completely, and changes in absorbance dependent upon the TG concentration in the sample mixture liquid was able to be detected.

As described, in this embodiment, the same effects as in Embodiment 1 can be obtained because: the disc main body 20 includes the liquid sample reserve unit 23, the reagent chamber 40, and the measurement chamber 25; the reagent chamber 40 is formed so that the reagent chamber 40 is allowed to be orthogonal to centrifugal force direction X, the length in the direction where the solid reagents 30 are disposed are extended longer than centrifugal force direction X, the width in the direction substantially parallel to centrifugal force direction X is set larger than the width of the solid reagent 30, and the depth is substantially equal to the height of the solid reagent 30; the liquid sample in an amount corresponding to one solid reagent 30 is supplied to the reagent chamber 40 from the liquid sample reserve unit 23; and the liquid sample and the solid reagent 30 are mixed in the reagent chamber 40 by spinning the disc main body 20 to supply the sample mixture liquid to the measurement chamber 25.

In the above-mentioned Embodiments 1 and 2, in the example shown, changes in the absorbance of WST-9, which is pigment, are detected to measure the TG concentration in plasma. The present invention may also be suitably used, in addition to the above-mentioned, for example, for a measurement using a solid reagent containing potassium ferricyanide instead of WST-9. In such a measurement, at least an electrode that functions as a counter electrode and an electrode that functions as a working electrode are provided in the measurement chamber 25 of the sample-liquid analysis disc. Further, in the disc main body 20, terminals for the electric contact to the above electrodes from outside the disc main body 20 are provided. By using such a sample-liquid analysis disc, for example, to ferrocyanide ions which are produced by reduction of ferricyanide ions, a voltage is applied between such electrodes and current generated at reoxidation is measured, to determine the TG concentration.

In this case, in which ferricyanide ions are reduced by oxidation of glycerol in plasma, instead of potassium ferricyanide, a redox compound that is capable of electron transfer with NADH may be arbitrary used. The redox compound is not particularly limited, as long as it is capable of the electron transfer to and from NADH produced by the reduction of NAD under the reaction conditions that allow redox reaction between glycerol and NAD. For example, 1-methoxy-5-methylphenazinium sulfate, Meldora blue, and 1,2-naphthoquinone-4-sulfonic acid (1,2-Naphtoquinone-4-sulfonate) may be mentioned.

Other than TG contained in plasma, the present invention can also be applied for an arbitrary measurement target, in the case when the changes in the concentration of a specific component in a reaction system including the measurement target can be detected optically or electrochemically.

The shape of the solid reagent 30 is not limited to substantially semi-spherical, and may be spherical, cylindrical, or polyhedron. The solid reagent 30 may include sugar or protein in such a range that gives no effect to the reaction for improving physical strength. The reagent may be used singly or in combination for forming the solid reagent 30.

Each chamber in the sample-liquid analysis disc in the embodiments, which is configured with the upper base board, the lower base board, and the spacer, may be configured with other members, and provided on a disc-like member; and each chamber may be configured with the upper base board, the lower base board, and the spacer, and the disc itself may be configured with the upper base board, the lower base board, and the spacer. The chamber configured with the upper base board, the lower base board, and the spacer may be placed inside the disc, or may be placed on the disc. In FIGS. 1 and 2, each chamber is configured with the upper base board, the lower base board, and the spacer, and is placed in the disc.

INDUSTRIAL APPLICABILITY

The present invention is useful for a sample-liquid analysis disc in which a sample such as blood is analyzed by mixing a liquid sample supplied in the disc main body and a solid reagents disposed in the disc main body to bring to action, and detecting the chemical reaction of the sample mixture liquid; and for a method for analyzing a sample mixture liquid.

The invention claimed is:

1. A sample-liquid analysis disc for analyzing a sample solution comprising:
   a solid reagent;
   a disc main body; and
   at least one sample mixing unit provided at said disc main body, wherein said sample mixing unit comprises:
   a liquid sample reserve unit for reserving a liquid sample;
   a reagent chamber connected to said liquid sample reserve unit via a first flow path, and formed so that said solid reagent can be disposed in a plural number, and to which said liquid sample is supplied, from said liquid sample reserve unit via said first flow path by centrifugal force caused by at least a spin of said disc main body;
   a measurement chamber connected to said reagent chamber via a second flow path, and to which a sample solution containing said liquid sample and said solid reagent mixed in said reagent chamber is supplied by centrifugal force caused by the spin of said disc main body and capillarity generated in said second flow path;
   wherein said reagent chamber is formed so that said solid reagent can be disposed in a plural number, in a direction substantially parallel to a radial direction of said disc in which said centrifugal force is generated, or in a direction substantially perpendicular to said radial direction;
   said reagent chamber comprises an upper base board, a lower base board, and a spacer interposed between said upper base board and said lower base board;
   said upper base board has a concave portion to contact a portion of said solid reagent;
   said spacer has a cutaway portion; and
   said solid reagent is fixed in a space formed by said cutaway portion and said concave portion.

2. The sample-liquid analysis disc in accordance with claim 1, wherein said reagent chamber is substantially rectangular having a long side and a short side, and formed so that said long side is substantially parallel to said radial direction, when seen in a direction of normal to a main surface of said disc.

3. The sample-liquid analysis disc in accordance with claim 1, wherein said reagent chamber is substantially rectangular having a long side and a short side, and formed so that said long side is substantially perpendicular to said radial direction, when seen in a direction of normal to a main surface of said disc.

4. The sample-liquid analysis disc in accordance with claim 1, wherein at least a portion of said solid reagent is fixed in said reagent chamber in a direction of normal to the main surface of said disc.

5. The sample-liquid analysis disc in accordance with claim 1, wherein said solid reagent is disposed in a plural number in said reagent chamber.

6. The sample-liquid analysis disc in accordance with claim 1, wherein said solid reagent is formed of freeze-dried granules.

7. A method for analyzing a sample mixture liquid using the sample-liquid analysis disc in accordance with claim 5, the method comprising:
   supplying a liquid sample to said liquid sample reserve unit in a volume corresponding to a volume of one solid reagent;
   supplying said liquid sample from said liquid sample reserve unit to said reagent chamber by centrifugal force by spinning said disc main body;
   mixing said liquid sample and said solid reagent in said reagent chamber by using centrifugal force and capillarity; and
   supplying said sample mixture liquid into said measurement chamber, to detect a chemical reaction of said sample mixture liquid in said measurement chamber.

8. The method for analyzing a sample mixture liquid in accordance with claim 7, wherein said detection is carried out optically.

9. A method for analyzing a sample mixture liquid using the sample-liquid analysis disc in accordance with claim 6, the method comprising:

supplying a liquid sample to said liquid sample reserve unit in a volume corresponding to a volume of one solid reagent;

supplying said liquid sample from said liquid sample reserve unit to said reagent chamber by centrifugal force by spinning said disc main body;

mixing said liquid sample and said solid reagent in said reagent chamber by using centrifugal force and capillarity; and supplying said sample mixture liquid into said measurement chamber, to detect a chemical reaction of said sample mixture liquid in said measurement chamber.

10. The method for analyzing a sample mixture liquid in accordance with claim 9, wherein said detection is carried out optically.

* * * * *